United States Patent
Graham

(10) Patent No.: US 8,460,343 B2
(45) Date of Patent: Jun. 11, 2013

(54) INTRAMEDULLARY TUBULAR BONE FIXATION

(75) Inventor: Thomas J. Graham, Baltimore, MD (US)

(73) Assignee: The Cleveland Clinic Foundation, Cleveland, OH (US)

( * ) Notice: Subject to any disclaimer, the term of this patent is extended or adjusted under 35 U.S.C. 154(b) by 847 days.

(21) Appl. No.: 12/571,502

(22) Filed: Oct. 1, 2009

(65) Prior Publication Data

US 2010/0082068 A1 Apr. 1, 2010

Related U.S. Application Data

(60) Provisional application No. 61/101,890, filed on Oct. 1, 2008.

(51) Int. Cl.
*A61B 17/80* (2006.01)
(52) U.S. Cl.
USPC .............................. 606/280; 606/62
(58) Field of Classification Search
USPC ................... 606/60, 62–64, 67, 280
See application file for complete search history.

(56) References Cited

U.S. PATENT DOCUMENTS

| 4,503,847 | A  | * | 3/1985 | Mouradian | 606/64 |
| 6,379,359 | B1 | * | 4/2002 | Dahners | 606/62 |
| 6,706,046 | B2 | * | 3/2004 | Orbay et al. | 606/62 |
| 6,730,090 | B2 | * | 5/2004 | Orbay et al. | 606/62 |
| 2006/0149257 | A1 | | 7/2006 | Orbay et al. | |
| 2006/0161156 | A1 | | 7/2006 | Orbay | |
| 2008/0114360 | A1 | | 5/2008 | Da Frota Carrera | |

FOREIGN PATENT DOCUMENTS

WO    WO87/04612    8/1987

* cited by examiner

*Primary Examiner* — Kevin T Truong
*Assistant Examiner* — Michael Araj
(74) *Attorney, Agent, or Firm* — Tarolli, Sundheim, Covell & Tummino LLP

(57) ABSTRACT

An intramedullary bone fixation device suitable for treatment of fractures of the tubular bones of the hand or feet. The implantable device can be used singly or introduced through both the radial and ulnar aspects. The device includes a stem having a tip portion at one end and a base member at the opposite end of the stem. The stem and tip portions are configured with a unique configuration and cross section to facilitate insertion into and through the canal and provide the necessary forces on the stem portion within the canal. The base is sized and configured to minimize tissue damage while as the same time providing a strong point of fixation.

19 Claims, 15 Drawing Sheets

INTRAMEDULLARY TUBULAR BONE FIXATION

This application claims the benefit of Provisional Patent Application No. 61/101,890, entitled, "Intramedullary Bone Fixation", filed on Oct. 1, 2008, the entire contents of which is hereby expressly incorporated by reference.

FIELD OF THE INVENTION

The present invention relates to the field of bone implants, and, more particularly, to bone fracture implants for long bones and related methods.

BACKGROUND OF THE INVENTION

Presently there are a number of approaches in use to treat complex fractures of the hand or foot. One common approach is the use of plating to provide the necessary internal fixation. One significant drawback to plating is the necessity to form a large incision in the vicinity of the fracture. In addition, the muscle, ligament and other sensitive tissue is often moved so as to provide access to the surface of the bone. The disturbance of these tissues can extend the time required for recuperation and rehabilitation. The plate is attached to one or more fragments in such as way so as to position the fracture in a proper alignment for healing. Due to the aforementioned drawbacks, plating is used primarily for those case where there is a need to stabilize complex fractures.

Where the bone fractures are less complex it is possible to treat the fracture with a cast. While casting is a more conservative approach this fixation technique may not produce sufficient immobilization of the fragments so as to result in a favorable outcome. Casting is generally not as effective when the fracture is oblique rather than transverse as the bone segments can move relative to one another resulting in a less than desirable outcome.

Other forms of bone fixation approaches include wiring the bone fragments together, pinning the bone fragments to a rigid metal frame positioned outside of the patient's body, and use of percutaneous pins that are inserted introfocally and subsequently connected to a rigid metal frame external to the body. These approaches tend to cause irritation of sensitive tissues, such as tendons, ligaments, muscle, and nerves and can results in irritation, pain, as well as infection due to incisions and open wounds adjacent the pins.

Although a large number of approaches are available to treat fractures, none to date provide a percutaneous intrafocal plate that is simple and safe to use and is an effective bone fixation device. Many fixation devices for use in stabilizing bone fractures lack the ability to easily, efficiently and safely and require an invasive approach which can result in increased pain, and infection for the patient and extended recuperation and rehabilitation time frames.

DESCRIPTION OF THE PRIOR ART

U.S. Pat. No. 6,379,359, to Dahners, discloses a plate apparatus for addressing metaphyseal and similar bone fractures. The apparatus comprises an elongated plate element having a flat plate surface at one end thereof defining a top surface and a bottom surface and a leading end and a trailing end. A longitudinally extending resilient body element depends from the trailing end of the flat surface and defines a shoulder at one end which joins the flat plate surface and an arcuate pin at the other end. The intrafocal plate is formed so that a force applied at the arcuate pin end causes a force to be applied in the opposite direction at the flat plate surface.

U.S. Pat. No. 6,730,090, to Orbay et al, discloses a fixation device that includes a proximal nail portion and a distal plate portion. The nail portion includes a flexible tapered section and a rigid distal section larger in diameter and is adapted to be inserted into a medullary canal of the fractured bone. The plate portion has a low, narrow profile and includes three longitudinally displaced peg holes, each of which is adapted to orient a peg in a different orientation from the others. The plate portion is adapted to be positioned on the outside of a fractured bone when the nail portion is within the medullary canal. The device provides the benefits of both an intramedullary nail and a bone plate in a single device.

U.S. Pat. No. 6,706,046, to Orbay et al, discloses a fixation device having a nail portion and a plate portion, preferably horizontally and vertically offset relative to the nail by a neck portion. The nail portion includes threaded screw holes, and the plate portion includes longitudinally displaced peg holes, each of which is adapted to orient a peg in a different orientation for the others. The system also includes unicortical screws having a reasonably large head adapted to seat against the outer surface of the bone and a threaded shaft adapted to engage in the peg holes. Bone is clamped between the nail portion and the head of the head of the unicortical screws. The pegs provide stabilization and support for subchondral fragments. Moreover, as the pegs preferably enter the subchondral fragments from a plurality of directions, additional fixation of the device into the bone is provided.

U.S. Published Patent Application No. 2006/0149257, to Orbay et al, is directed to a fracture fixation device that includes a plate portion and an intramedullary nail portion which is offset relative to the plate portion by a neck portion. The plate portion includes longitudinally displaced peg holes which orient pegs along an imaginary surface parallel to subchondral bone of an articular surface. The upper surface of the plate portion includes a dimple to reference a jig. The nail portion includes threaded screw holes oriented normal to an endosteal surface, and a smaller K-wire alignment hole parallel to the screw holes. The jig has a first portion which references with the dimple and second portion in alignment over the screw holes of the nail portion. The back portion of the first portion of the jig is curved upward to facilitate maneuvering of the jig. The first and second portions of the jig include K-wire guide holes which direct K-wires relative to holes in the device.

U.S. Published Application No. 2006/0161156, to Orbay, is directed to a fracture fixation device that includes a plate portion and an intramedullary nail portion which is offset relative to the plate portion by a neck portion. The plate portion overhangs the neck portion and includes longitudinally displaced holes which orient pegs along an imaginary surface parallel to subchonodral bone of an articular surface. The nail portion includes threaded screw holes oriented normal to an endosteal surface, and a smaller K wire alignment hole parallel to the screw holes. The back portion of the first portion of the jig is curved upward to facilitate maneuvering of the jig. The first and second portions of the jig include K-wire guide holes which direct K-wires relative to holes in the device.

SUMMARY OF THE INVENTION

In accordance with the present invention the bone fixation implant device is suitable for treatment of fractures of the tubular bones of the hand or feet. The implant can be used singly or introduced through both the radial and ulnar aspects.

The bone fixation implant implant device has been designed to be introduced though the collateral ligament regions of the phalanges, metacarpal and metatarsals. The implant can also be utilized by antegrade insertion. The device includes a stem having a tip portion at one end and a base member at the opposite end of the stem. The stem and tip portions are configured with a unique configuration and cross section to facilitate insertion into the canal and provide the necessary forces on the stem portion within the canal. The base is sized and configured to minimize tissue damage while as the same time providing a strong point of fixation.

Accordingly, it is an objective of the instant invention to provide an intramedullary bone fixation implant that can be percutaneously implanted for fixation of tubular bone of the hands and feet.

It is a further objective of the instant invention to provide a bone fixation device that can be implanted using minimally invasive techniques.

It is yet another objective of the instant invention to provide an implantable bone fixation device that can be inserted using a simplified process of open reduction internal fixation (ORIF) and enabling the treatment of moderately complex fractures by a single surgeon in venues where equipment and assistance may be modest.

It is a still further objective of the invention to provide an implantable bone fixation device configured with a geometry that affords instant stability thereby accelerating motion recovery.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
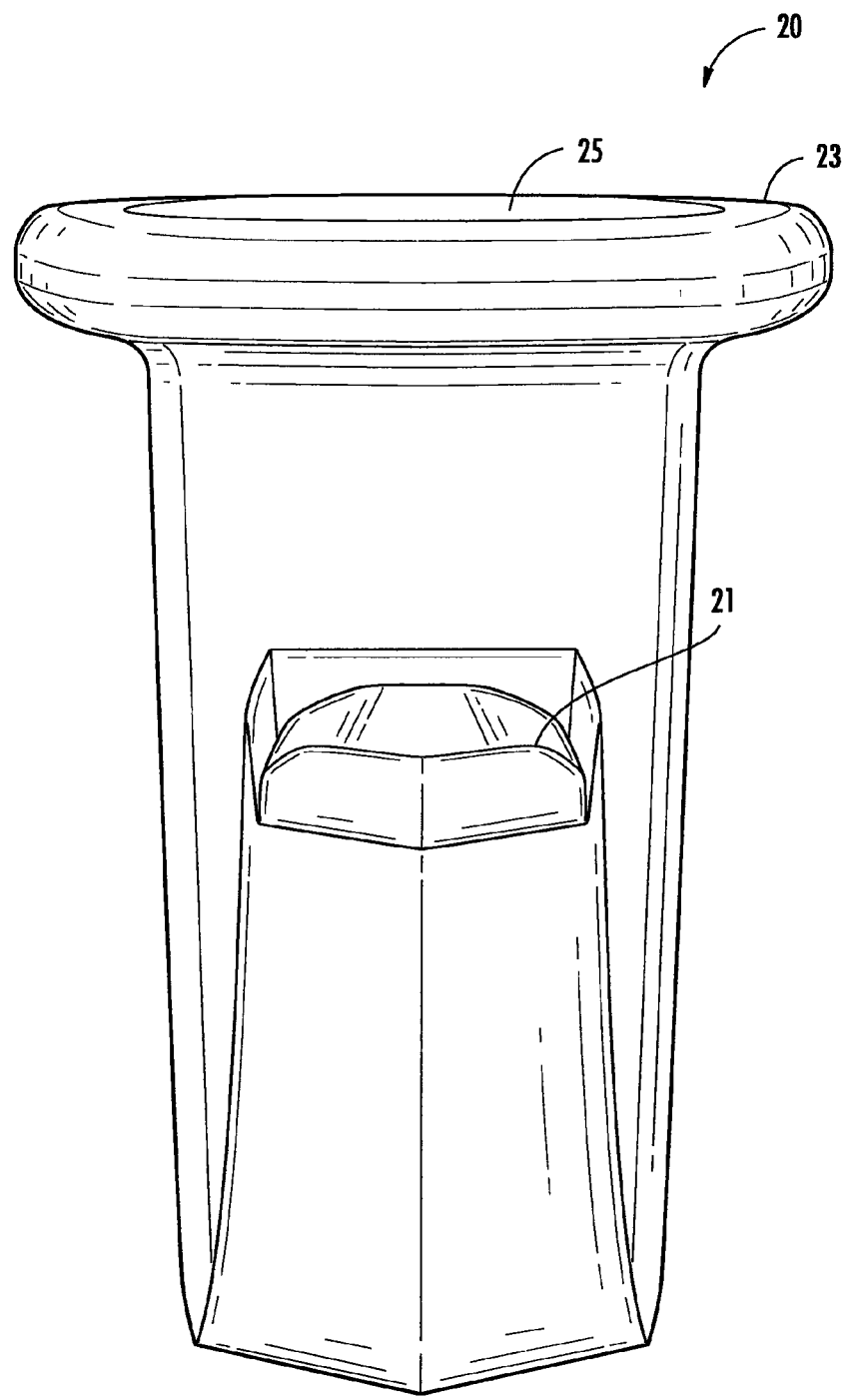
FIG. 1 is a front side view of the bone fixation implant according to the present invention.
Figure 2:
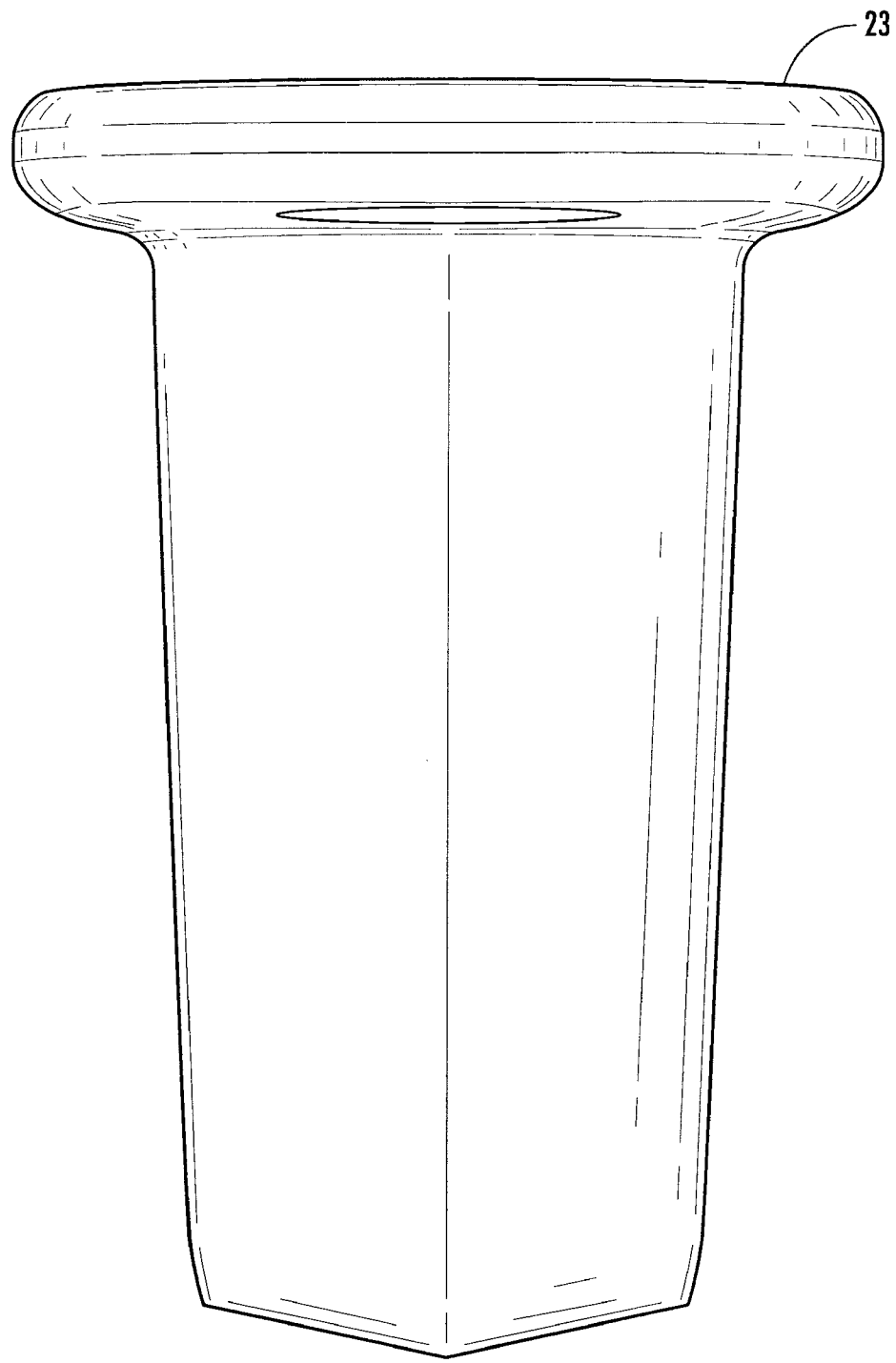
FIG. 2 is a backside view of the bone fixation implant of FIG. 1.
Figure 3:
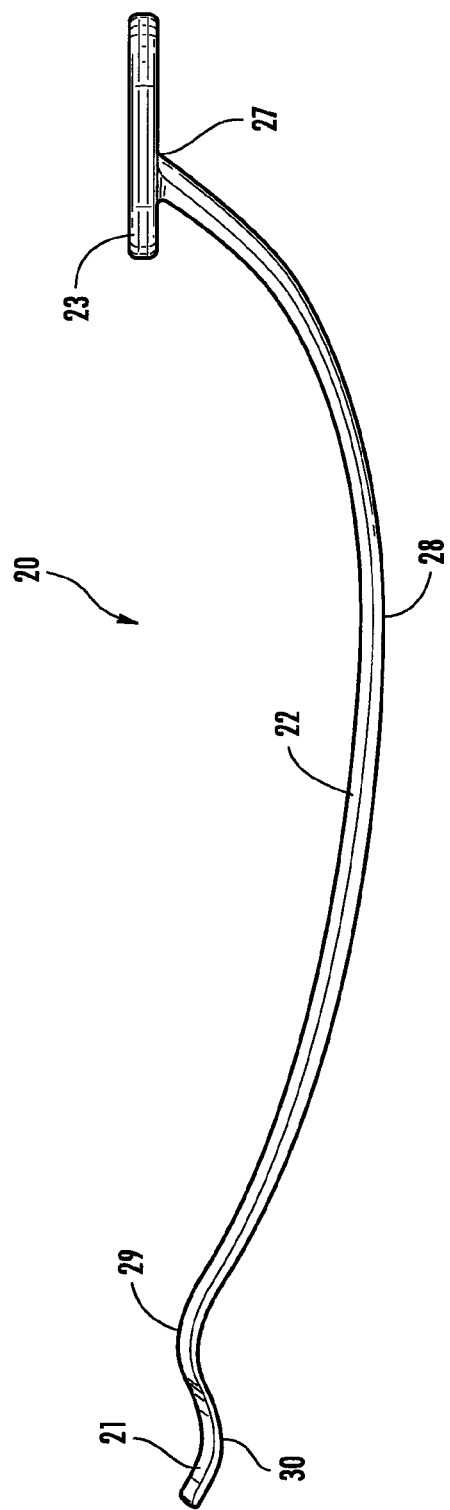
FIG. 3 is a side elevational view of the bone fixation implant of FIG. 1.
Figure 4:
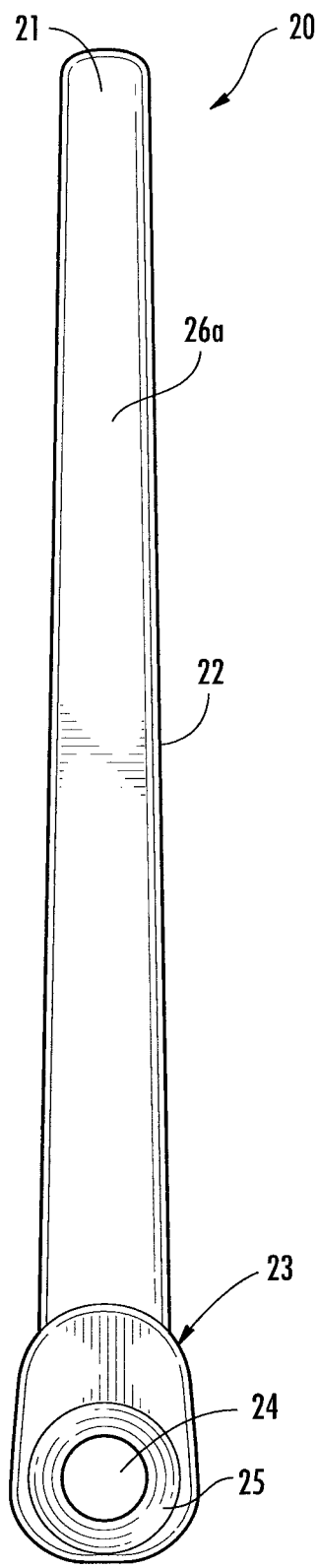
FIG. 4 is a top side plan view of the bone fixation implant of FIG. 1.
Figure 5:
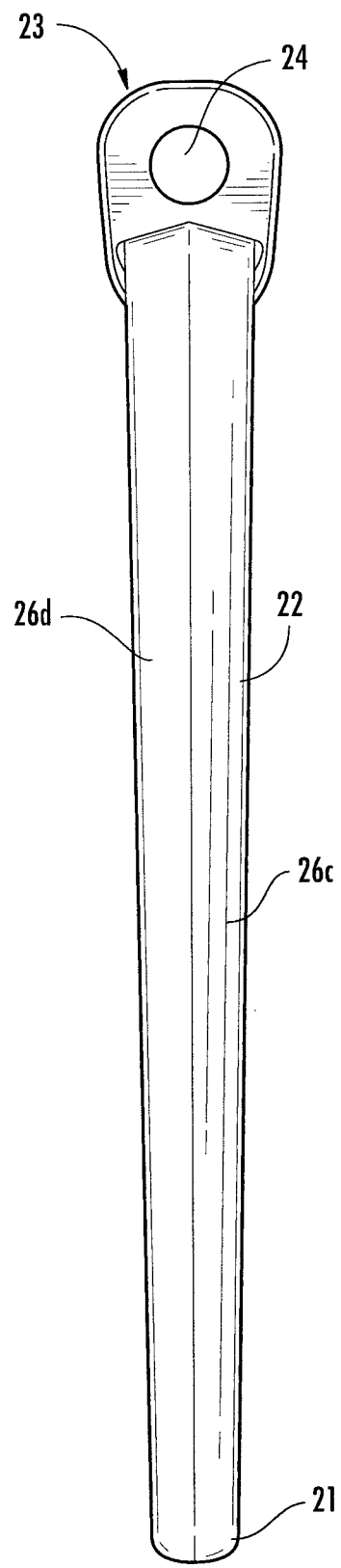
FIG. 5. is a bottom side plan view of the bone fixation implant of FIG. 1.
Figure 6:
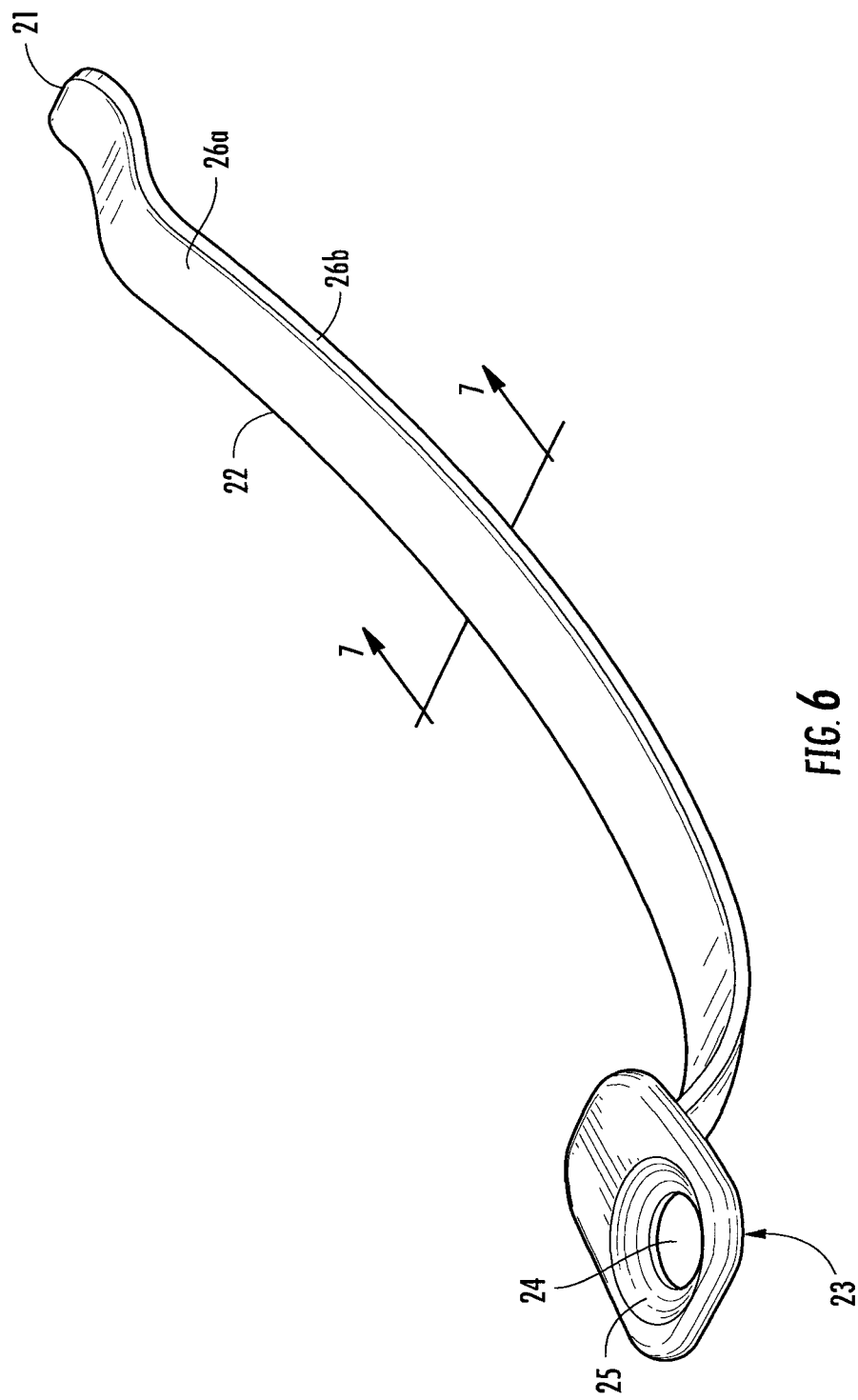
FIG. 6 is a perspective view of the bone fixation implant of FIG. 1.
Figure 7:
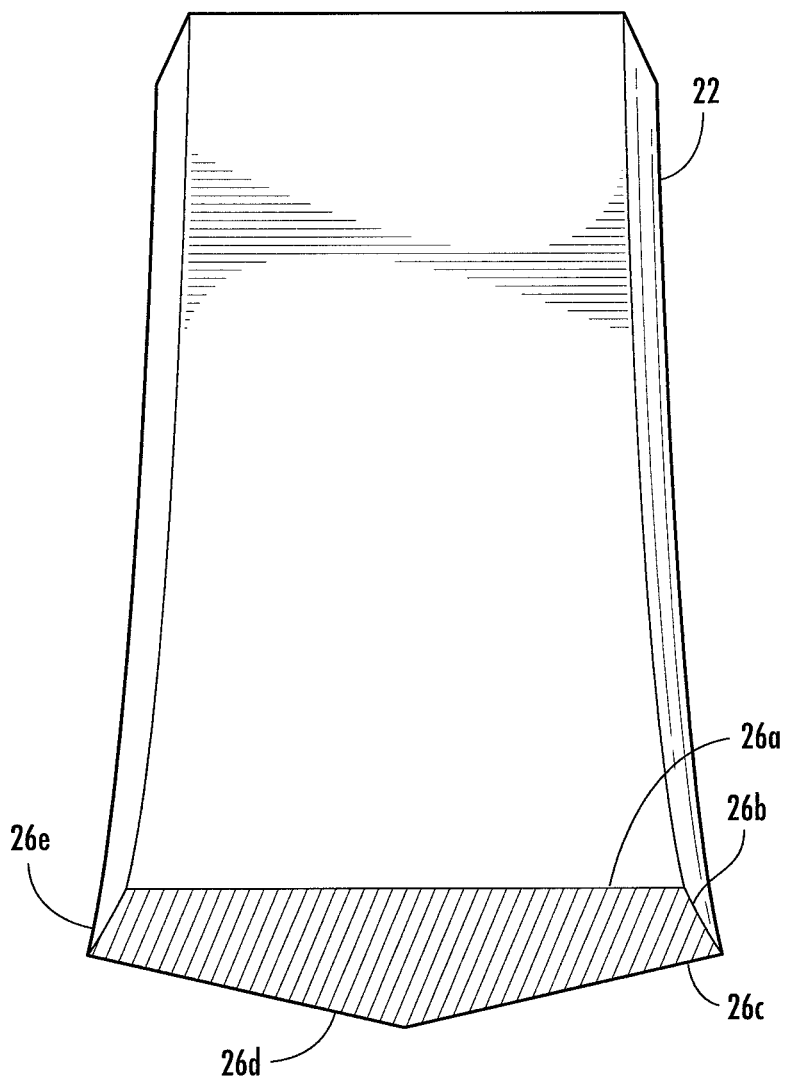
FIG. 7 is a cross-sectional view taken along line 7-7 of FIG. 6.

The present invention will now be described more fully hereinafter with references to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and multiple prime notation is used to indicate similar elements in alternative embodiments.

Referring initially to FIGS. 1-7, a bone fixation implant 20 according to the present invention is now described. The bone fixation implant 20 illustratively includes a stem 22, a tip 21 extending from a distal end of the stem, and a base 23 extending from a proximal end of the stem. The base 23 is coupled to the stem 22 via a joint 27 on the bottom side of the base 23. The base illustratively includes a fastener-receiving passageway 24 surrounded by a beveled edge 25 on the upper surface of base 23. While most fractures will require a single it should be understood that multiple head configurations can be used where appropriate. In addition, variable or fixed angle screw or screws can be utilized as the situation requires. As perhaps best seen in FIG. 7, the stem 22 has a cross-sectional pentagonal shape, having five discrete surfaces; 26a, 26b, 26c, 26d and 26e. Surface 26a is a first surface and extends longitudinally from the base 23 to the tip 21 as clearly shown in FIG. 4. The width of first surface 26 tapers as it approaches the tip end 21 of stem 22. Along each side of the first surface are edge surfaces 26b and 26e that extend longitudinally along the length of the first surface and are formed at an angle greater than 90 degrees with respect to the first surface. A second surface 26d and third surface 26c are located on the side of the stem opposite the first surface 26a as is clearly shown in FIG. 5. Second surface 26d extends longitudinally from base 23 to the tip 21 having a first side portion contiguous with edge surface 26e and a second side portion contiguous with third surface 26c. The opposite side portion of third surface 26c is contiguous with edge surface 26b. The stem 22 as viewed from the side in FIG. 3 has a concavo-convex profile. It is includes a first arcuate portion 28 that extends from joint 27 that terminates when it transitions into a second arcuate portion 29. Second arcuate portion 29 is curved is a direction diametrically opposed to the first arcuate portion 28. Second arcuate portion 29 terminates when in transitions into a third arcuate portion 30. Third arcuate portion 30 is curved in a direction diametrically opposite to the second arcuate portion 29 and similar to the first arcuate portion 28. The third arcuate portion terminates at the tip 21. The bone plate implant 20 may comprise metal suitable for surgical implantation, for example. The bone fixation implant 20 and fastener receiving aperture 24 can be formed in a variety of sizes to suit the particular application.

As will be appreciated by those skilled in the art, the bone fixation implant 20 may be used to treat fractures, for example, a spiral fracture, of the long bones, for example, the phalanges, metacarpals, or metatarsal. During implantation, the tip 21 is inserted through a damaged or cracked portion of the fractured bone and into the intramedullary canal/cavity. The tip configuration permits facile introduction and passage through the canal while the concavo-convex design results in a three point bending relationship with the canal. The pentagonal cross section of the stem 22 is designed to increase the surface area and strength of the stem. The base 23 is positioned on the extramedullary surface of the bone and affixed thereon by inserting a fastener through the fastener-receiving passageway 24, for example, a surgical screw. The ability to secure the implant with a screw or screws will maintain the location and the force on the stem portions located within the canal. Once implanted, the tip 21 applied outward pressure on the surfaces of the intramedullary canal, thereby aiding in fixation treatment of the fractured bone. Multiple implants can be employed to stabilize a given fracture.

Figure 8:
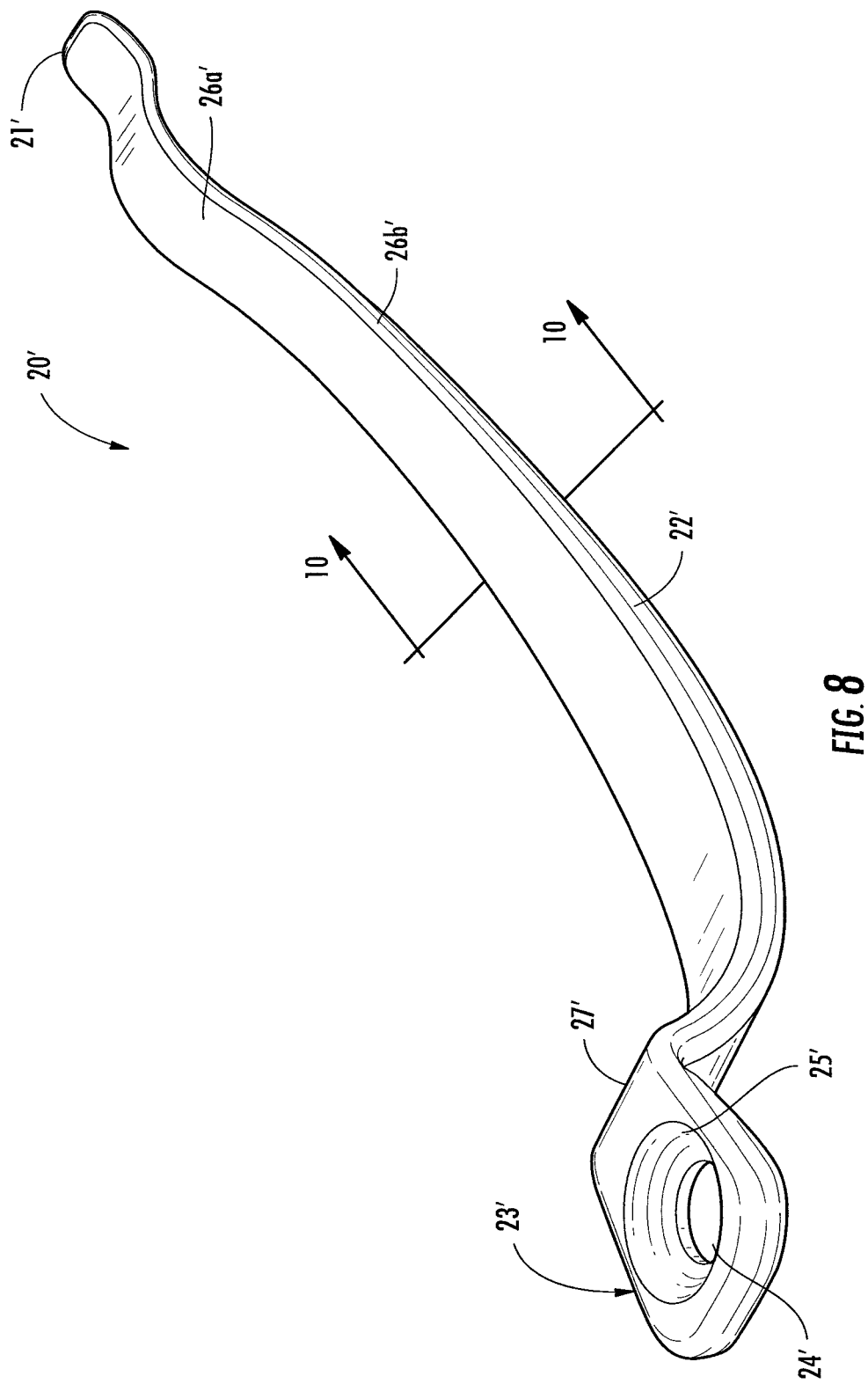
FIG. 8 is a perspective view of another embodiment of the bone fixation implant according to the present invention.
Figure 9:
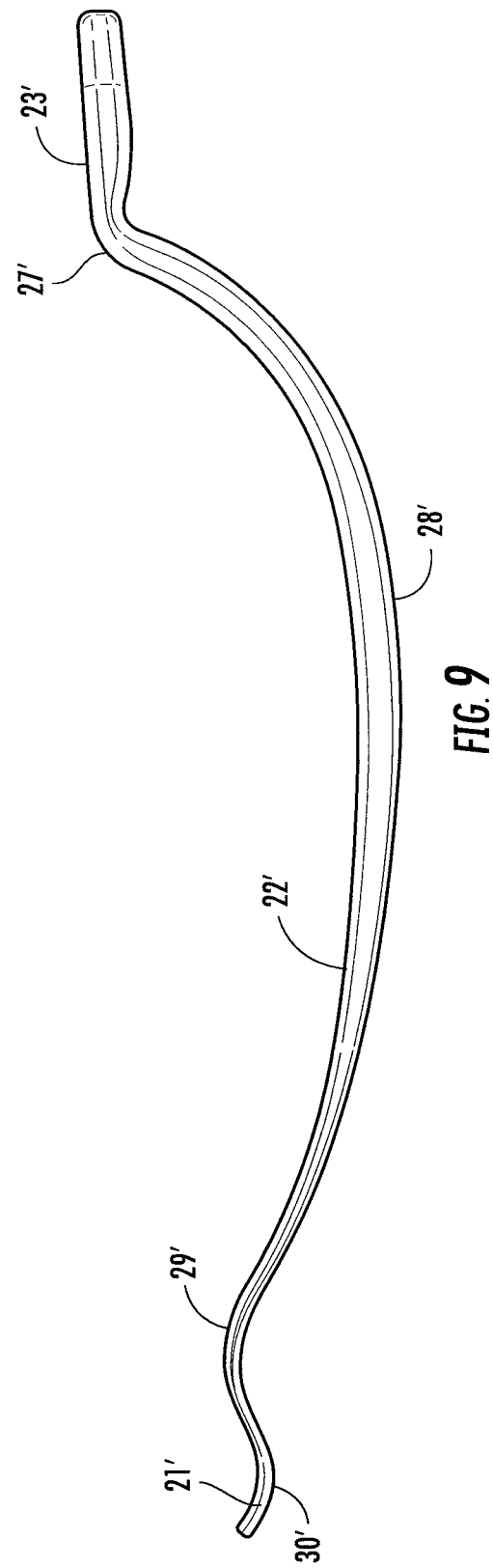
FIG. 9 is a side elevational view of the bone fixation implant of FIG. 8.
Figure 10:
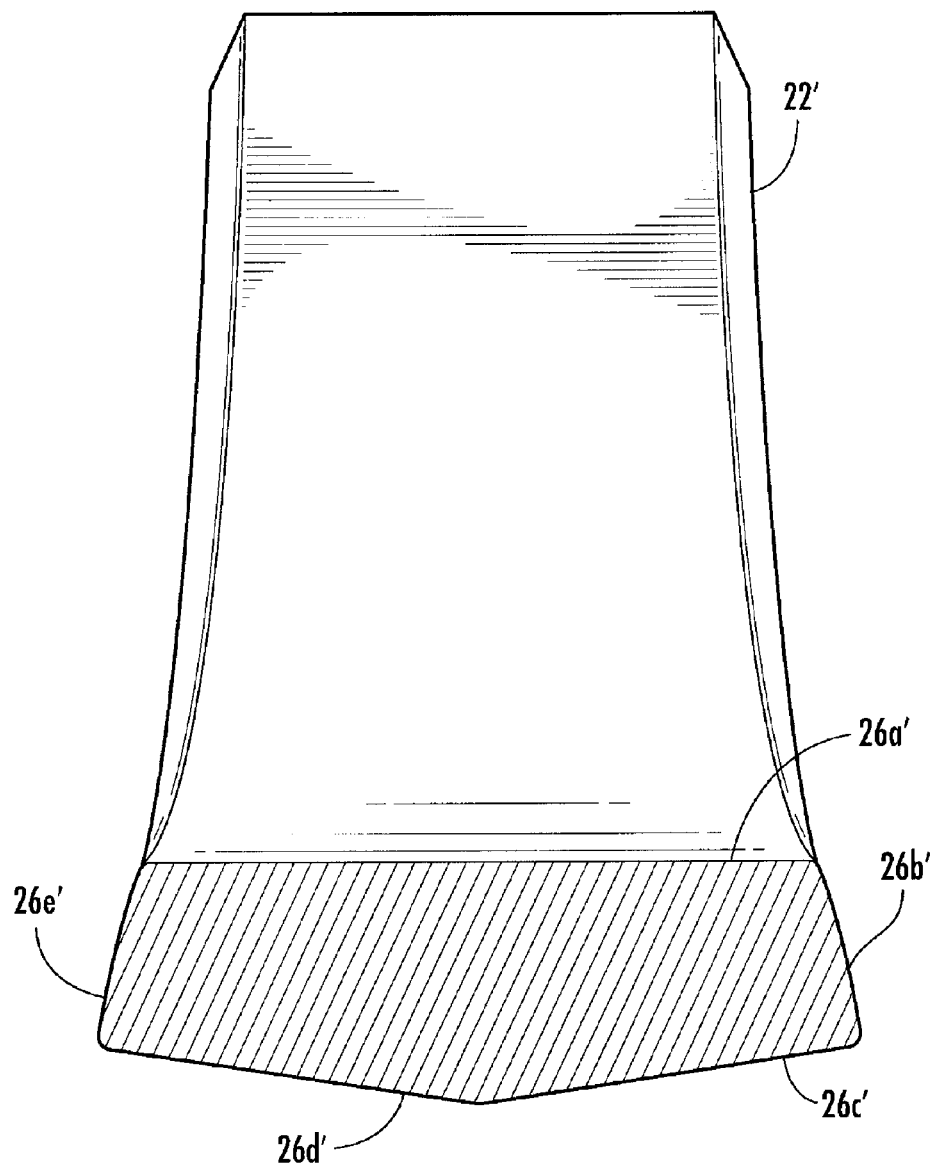
FIG. 10 is a cross-sectional view taken along line 10-10 of FIG. 8.

Referring now to FIGS. 8-10, another embodiment of the bone fixation implant 20' is now described. In this embodiment of the bone fixation implant 20', those elements already discussed above with respect to FIGS. 1-7 are given prime notation and most require no further discussion herein. This embodiment differs from the previous embodiment in that the base 23' is integrally formed the stem 22' via a curved bend 27' rather than a joint on the bottom side of the base 23'. Moreover, the stem 22' has a greater thickness for providing mechanical robustness. As perhaps best seen in FIG. 10, the stem 22' has a cross-sectional pentagonal shape, having five discrete surfaces; 26a', 26b', 26c', 26d' and 26e'. Surface 26a' is a first surface and edge surface 26b' extend longitudinally from the base 23 to the tip 21 as clearly shown in FIG. 8. The stem 22' as viewed from the side in FIG. 9 has a concavo-convex profile. It is includes a first arcuate portion 28' that extends from joint 27' that terminates when it transitions into a second arcuate portion 29'. Second arcuate portion 29' is curved is a direction diametrically opposed to the first arcuate portion 28'. Second arcuate portion 29' terminates when in transitions into a third arcuate portion 30'. Third arcuate portion 30' is curved in a direction diametrically opposite to the second arcuate portion 29' and similar to the first arcuate portion 28'.

Figure 11:
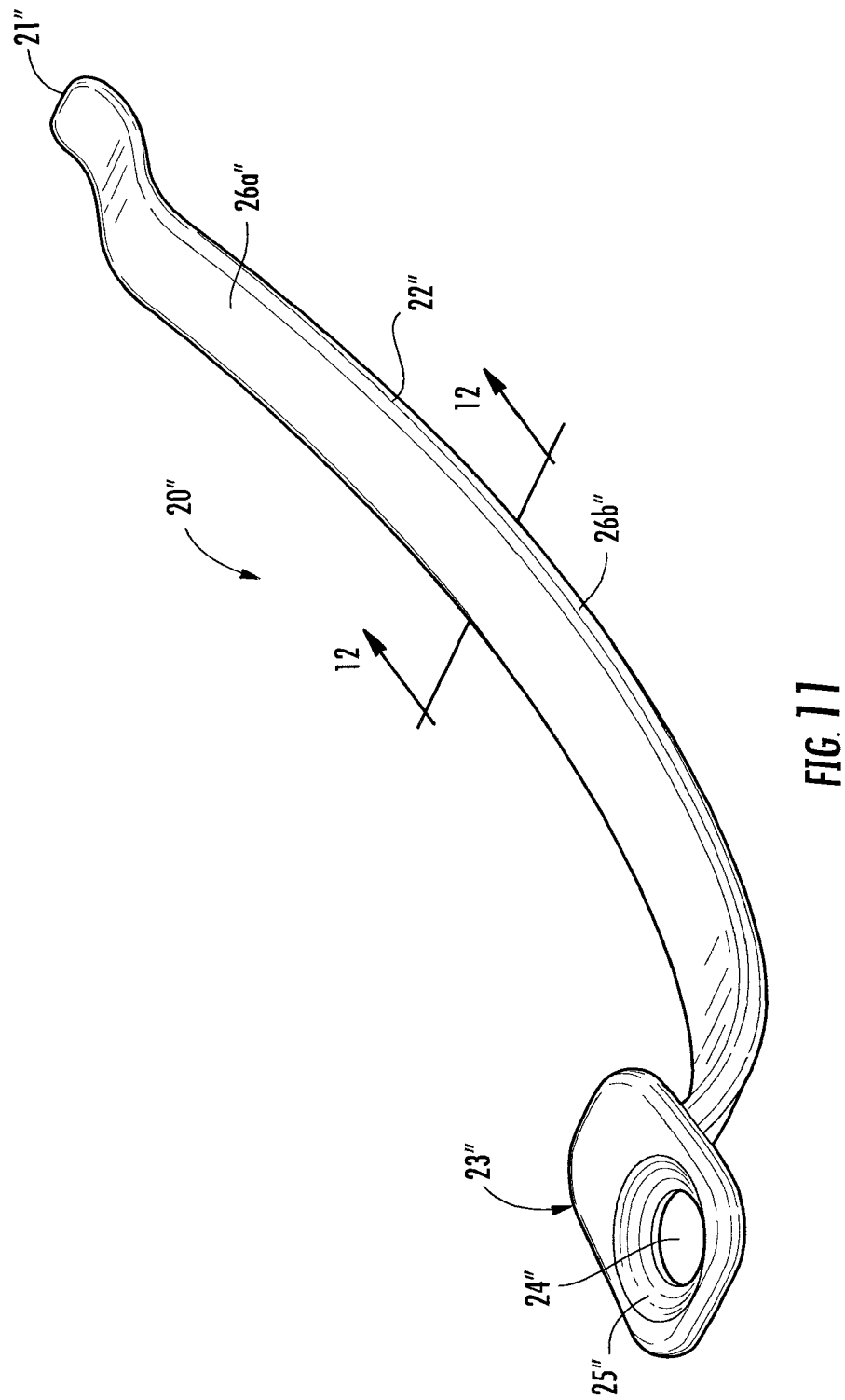
FIG. 11 is a perspective view of yet another embodiment of the bone fixation implant according to the present invention.
Figure 12:
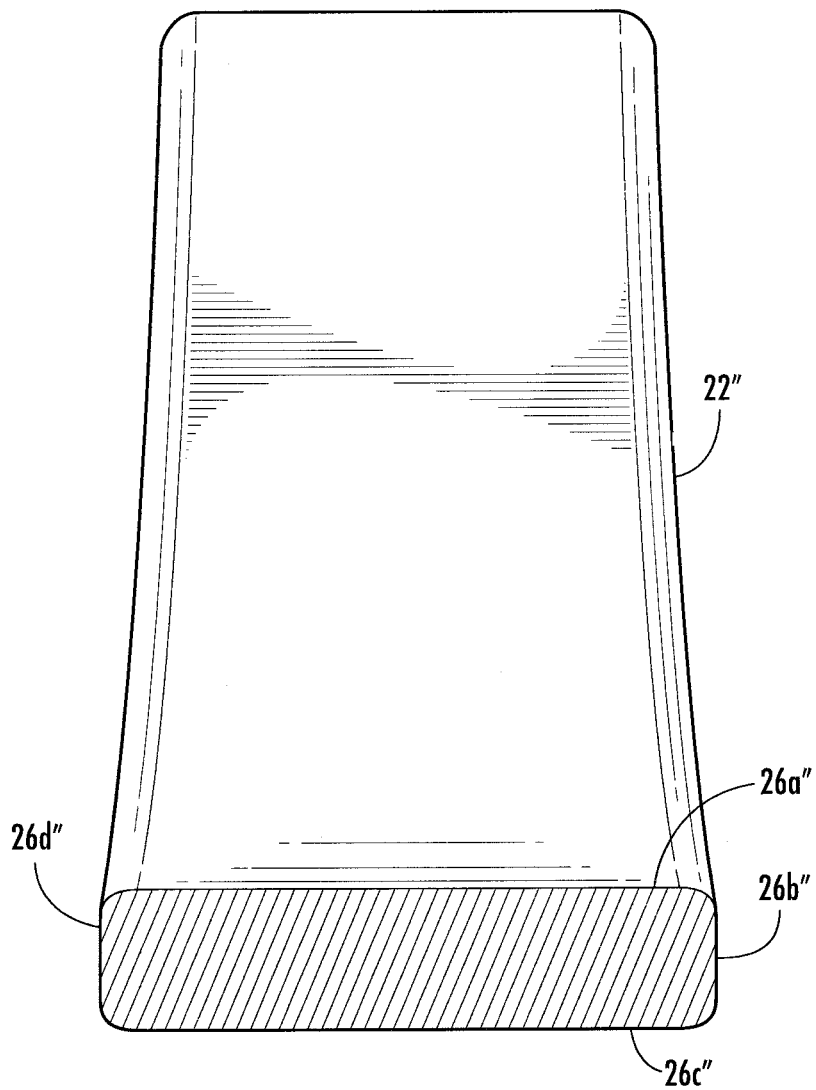
FIG. 12 is a cross-sectional view taken along line 12-12 of FIG. 11.

Referring now to FIGS. 11-12, another embodiment of the bone plate implant 20" is now described. In this embodiment of the bone fixation implant 20", those elements already discussed above with respect to FIGS. 1-7 are given double prime notation and most require no further discussion herein. As perhaps best seen in FIG. 12, this embodiment differs from the previous embodiment in that the stem 22" differently has a rectangular shape, i.e. the stem 22" has four sides 26a"-26c". The corners contiguous with adjacent sides are rounded to permit facile introduction and ease of passage into and through the canal.

Figure 13:
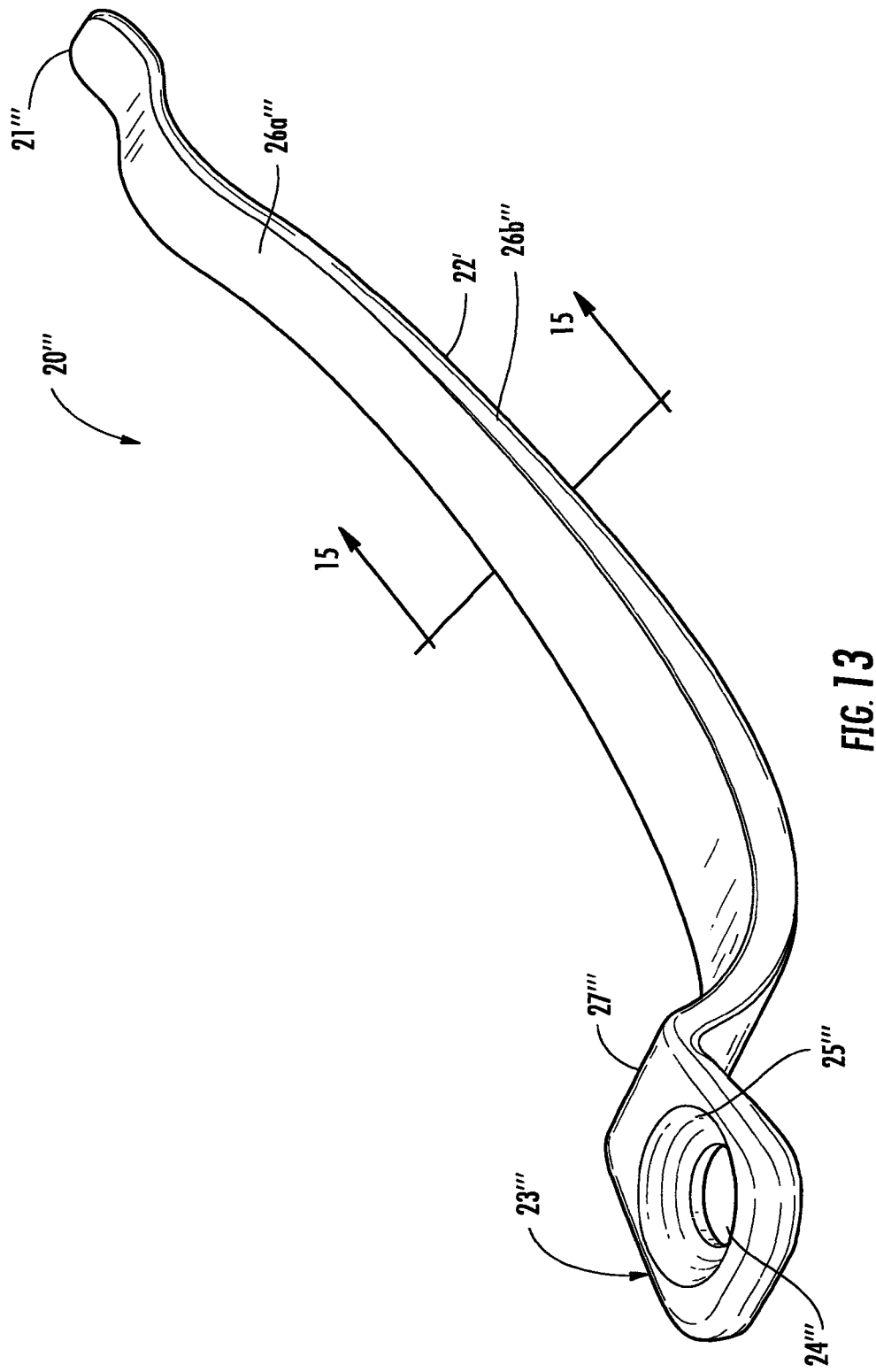
FIG. 13 is a perspective view of another embodiment of the bone fixation implant according to the present invention.
Figure 14:
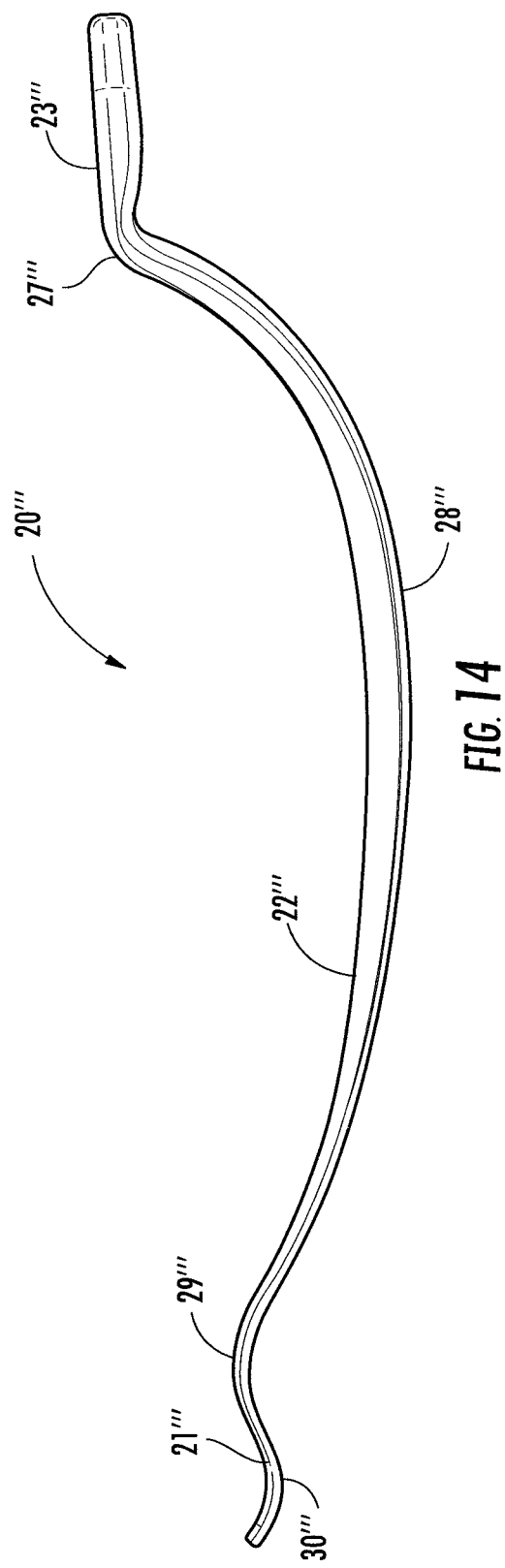
FIG. 14 is a side elevational view of the bone fixation implant of FIG. 13.
Figure 15:
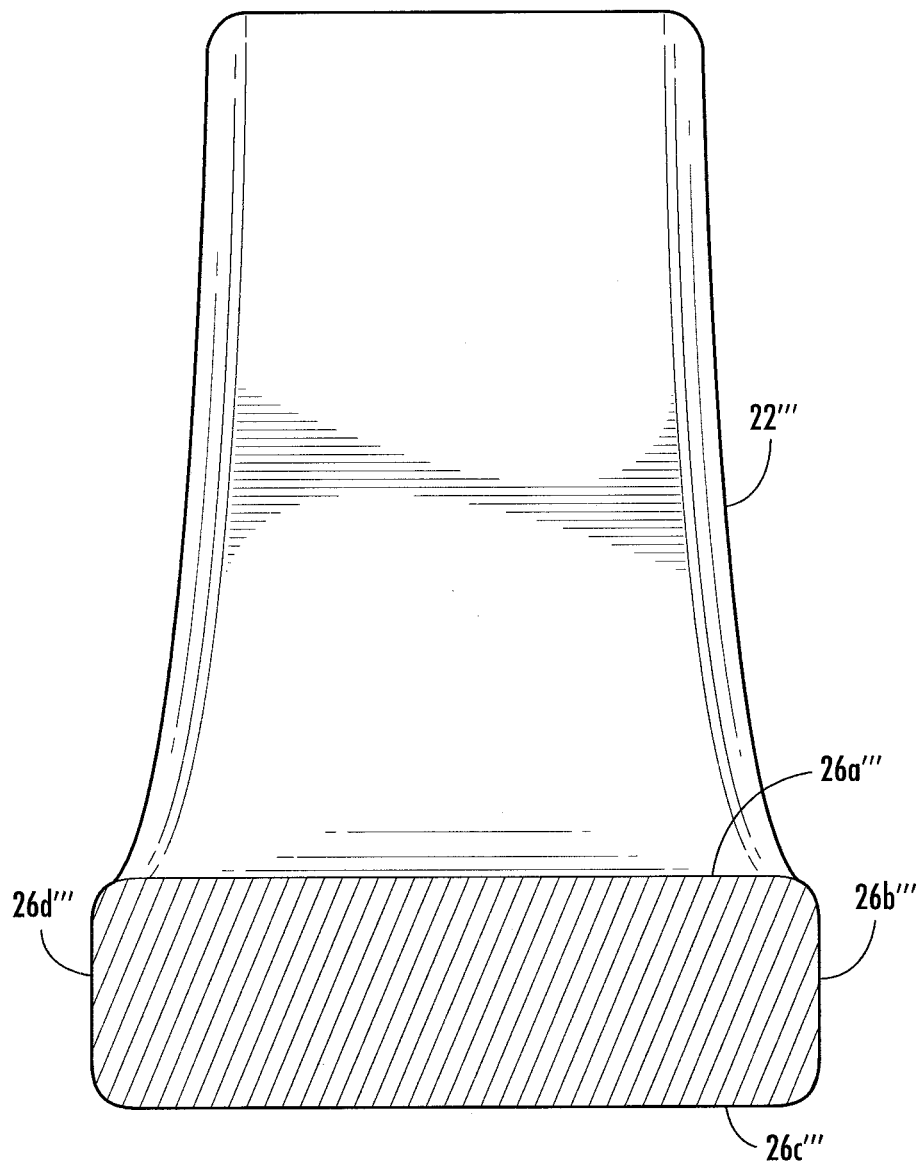
FIG. 15 is a cross-sectional view taken along line 15-15 of FIG. 13.

Referring now to FIGS. 13-15, another embodiment of the bone plate implant 20''' is now described. In this embodiment of the bone fixation implant 20''', those elements already discussed above with respect to FIGS. 1-7 are given triple prime notation and most require no further discussion herein. As perhaps best seen in FIG. 15, this embodiment differs from the previous embodiment in that the stem 22''' differently has a cross-sectional rectangular shape, i.e. the stem 22''' has four sides 26a'''-26c'''. Moreover, the base 23''' is formed to include the stem 22''' via a curved bend 27''' rather than a joint on the bottom side of the base 23'''. Moreover, the stem 22''' has a greater thickness for providing mechanical robustness. The corners contiguous with adjacent sides are rounded to permit facile introduction and ease of passage into and through the canal. The stem 22''' as viewed from the side in FIG. 14 has a concavo-convex profile. It is includes a first arcuate portion 28''' that extends from joint 27''' that terminates when it transitions into a second arcuate portion 29'''. Second arcuate portion 29''' is curved is a direction diametrically opposed to the first arcuate portion 28'''. Second arcuate portion 29''' terminates when in transitions into a third arcuate portion 30'''. Third arcuate portion 30''' is curved in a direction diametrically opposite to the second arcuate portion 29''' and similar to the first arcuate portion 28'''.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An implant for bone fracture fixation comprising: a base member including a fastener receiving passageway extending between a top and bottom surface of said base member; and a stem member being free of passageways and extending longitudinally from said base member, said stem member having a first end adjacent the base member and a second end at the opposite end thereof forming a tip of said stem, said stem having a concavo-convex profile including first, second and third arcuate portions, whereby the concavo-convex profile is adapted to result in a three point bending relationship within a canal of said bone; wherein the first arcuate portion extends downward from the base member to a first location on the body of the stem member longitudinally spaced from the base member, the first arcuate portion extending upward from the first location and terminating at a second location on the body of the stem member that is longitudinally spaced from the base member.

2. The implant according to clam 1, wherein:
the first arcuate portion of said stem extends from a point adjacent to said base member and terminates while transitioning into a second arcuate portion, said second arcuate portion being curved in a direction diametrically opposed to said first arcuate portion, said second arcuate portion terminates while transitioning into a third arcuate portion, said third arcuate portion being curved in a direction diametrically opposite to said second arcuate portion and similar to the first arcuate portion, said third arcuate portion terminating at said tip.

3. The implant according to claim 2, wherein said stem has a cross section including a width and thickness, the width of said stem decreasing in size from the point adjacent the base to the tip of said stem.

4. The implant according to claim 3, wherein said stem is connected to said base by a joint.

5. The implant according to claim 4, wherein said stem has a pentagonal cross section.

6. The implant according to claim 4, wherein said stem has a rectangular cross section.

7. The implant according to claim 3, wherein said stem is formed as a unitary member with said base and a curved bend forms a transition between said base and said stem.

8. The implant according to claim 7, wherein said stem has a pentagonal cross section.

9. The implant according to claim 7, wherein said stem has a rectangular cross section.

10. The implant according to claim 1, wherein each of the first, second, and third arcuate portions is substantially curved along each of their entire lengths.

11. An implant for bone fracture fixation comprising:
a base member including a fastener receiving passageway extending between a top and bottom surface of the base member; and
a stem member extending longitudinally from the base member, the stem member having a first end adjacent the base member and a second end at the opposite end thereof forming a tip of the stem, the stem having a concavo-convex profile including first, second and third arcuate portions, whereby the concavo-convex profile is adapted to result in a three point bending relationship within a canal of a bone, each of the first, second, and third arcuate portions being substantially curved in the longitudinal direction along each of their entire lengths.

12. The implant according to clam 11, wherein the first arcuate portion of the stem extends from a point adjacent to the base member and terminates while transitioning into a second arcuate portion, the second arcuate portion being curved in a direction diametrically opposed to the first arcuate portion, the second arcuate portion terminates while transitioning into a third arcuate portion, the third arcuate portion being curved in a direction diametrically opposite to the second arcuate portion and similar to the first arcuate portion, the third arcuate portion terminating at the tip.

13. The implant according to claim 12, wherein the stem has a cross section including a width and thickness, the width of the stem decreasing in size from the point adjacent the base to the tip of the stem.

14. The implant according to claim 13, wherein the stem is connected to the base by a joint.

15. The implant according to claim 14, wherein the stem has one of a pentagonal and rectangular cross section.

16. The implant according to claim 13, wherein the stem is formed as a unitary member with the base and a curved bend forms a transition between the base and the stem.

17. The implant according to claim 11, wherein the stem is free of passageways.

18. The implant according to claim 11, wherein the first arcuate portion extends downward from the base member to a first location on the body of the stem member longitudinally spaced from the base member, the first arcuate portion extending upward from the first location and terminating at a second location on the body of the stem member that is longitudinally spaced from the base member.

19. An implant for bone fracture fixation comprising:
a substantially planar base member including a single fastener receiving passageway extending between a top and bottom surface of the base member; and
a stem member extending longitudinally from the base member, the stem member having a generally uniform, contiguous body, the stem member having a first end adjacent the base member and a second end at the opposite end thereof forming a tip of the stem member, the stem member having a concavo-convex profile including:
a first arcuate portion extending downward from the base member to a first location on the body of the stem member longitudinally spaced from the base member, the first arcuate portion extending upward from the first location and terminating at a second location on the body of the stem member that is longitudinally spaced from the base member;
a second arcuate portion extending downward from the second location on the body of the stem member and terminating at a third location on the body of the stem member longitudinally spaced from the base member, the second arcuate portion being curved in a direction diametrically opposed to the first arcuate portion; and
a third arcuate portion extending upward from the third location on the body of the stem member and terminating at the tip of the stem member, the third arcuate portion being curved in a direction diametrically opposite to the second arcuate portion and similar to the first arcuate portion,
the first location on the body of the stem member being spaced at a greater longitudinal distance from the base member than the third location on the body of the stem member, the third location on the body of the stem member being spaced at a greater longitudinal distance from the base member than the second location on the body of the stem member.

* * * * *